United States Patent [19]

Secher

[11] Patent Number: 4,514,507

[45] Date of Patent: Apr. 30, 1985

[54] ASSAY FOR INTERFERON

[76] Inventor: David S. Secher, 2, Nightingale Ave., Cambridge CB1 4SQ, England

[21] Appl. No.: 396,911
[22] PCT Filed: Nov. 9, 1981
[86] PCT No.: PCT/GB81/00239
§ 371 Date: Jun. 28, 1982
§ 102(e) Date: Jun. 28, 1982
[87] PCT Pub. No.: WO82/01773
PCT Pub. Date: May 27, 1982

[30] Foreign Application Priority Data

Nov. 7, 1980 [GB] United Kingdom ............... 8035884

[51] Int. Cl.³ ........................................... G01N 33/54
[52] U.S. Cl. ........................................ 436/518; 435/7; 435/68; 435/810; 435/811; 260/112 R; 424/85; 436/531; 436/548
[58] Field of Search ............... 436/548, 86, 518–535, 436/815, 808, 536–542, 804, 823–824; 435/4, 7, 68, 70, 172, 240, 811, 948; 424/1.1, 8, 12, 85, 177; 260/112 R

[56] References Cited

U.S. PATENT DOCUMENTS

| | | | |
|---|---|---|---|
| 3,867,517 | 2/1975 | Ling | 436/531 |
| 4,016,043 | 4/1977 | Schuurs | 435/7 |
| 4,098,876 | 7/1978 | Piasio | 436/500 |
| 4,172,124 | 10/1979 | Koprowski et al. | 424/85 |
| 4,196,265 | 4/1980 | Koprowski et al. | 435/2 |
| 4,244,940 | 1/1981 | Jeong et al. | 436/500 |
| 4,376,110 | 3/1983 | David et al. | 436/513 |
| 4,423,147 | 12/1983 | Secher et al. | 435/68 |

FOREIGN PATENT DOCUMENTS

WO81/02899 10/1981 PCT Int'l Appl. .
8012096 4/1980 United Kingdom .

OTHER PUBLICATIONS

Staehelin, T. et al., Methods in Enzymology, (1981), vol. 78, pp. 505–512; vol. 79, pp. 589–595.
Staehelin, T. et al., Symposium Giovanni Lorenzini Foundation, vol. 11, pp. 79–85, (1981).
Rodbard, D. et al., Immunochemistry, vol. 15, pp. 71–76, (1978).
Miles, L. E. M., Ricerca in Clinicae in Laboratorio, vol. 5, pp. 59–72, (1975).
Secher, D. S. et al., Nature, vol. 285 (5765), pp. 446–450, (1980).
Montagnier, L. et al., C. R. Seances Acad. Sci. Ser. D., vol. 291 (11), pp. 893–896, (1980).
Staehelin, T. et al., Proceedings of the National Academy of Sciences, U.S.A., vol. 78 (3), pp. 1848–1852, (1981).
Morser, J. et al., Journal of General Virology, vol. 53 (2), pp. 257–265, (1981).
Stefanos et al., J. Gen. Virology, vol. 50, pp. 225–229, (1980).
Secher, D. S., Nature, vol. 290, pp. 501–503, (1981).
Andzhaparidze, O. G. et al., Vopr. Virusol., vol. 1, pp. 44–47, (1981).

Primary Examiner—Benjamin R. Padgett
Assistant Examiner—M. Moskowitz
Attorney, Agent, or Firm—Cushman, Darby & Cushman

[57] ABSTRACT

An assay for interferon comprises two antibodies to interferon, one labelled and at least one being a monoclonal antibody. The non-labelled antibody is suitably attached to a solid support such as polystyrene beads and the labelled antibody is suitably a radiolabelled monoclonal antibody, e.g. 125 I-NK2.

18 Claims, 3 Drawing Figures

ASSAY FOR INTERFERON

FIELD OF THE INVENTION

This invention relates to the field of immunometric assays. In particular it relates to an antibody excess immunometric assay for interferon involving the use of monoclonal antibody to interferon.

BACKGROUND OF THE INVENTION

The interferons are a group of related proteins present in the mammalian body. An interferon is a protein factor which exerts virus non-specific, antiviral activity at least in homologous cells through cellular metabolic processes involving synthesis of both RNA and protein. The interferons are classified into types on the basis of antigenic specificity, the designations being alpha, beta and gamma (these correspond to previous designations leucocyte, fibroblast and type II (immune) interferons respectively). In addition to its antiviral effect interferon has been implicated as a mediator or immune function of other cellular phenomena. Interferon research has been hampered by problems in its assay. The only widespread assays use tissue cultured cells and compare some parameter of viral growth (for example viral RNA synthesis or host cell death) in the presence and absence of interferon. These complex biological assays, though sensitive, are laborious and subject to inherent variability. In particular, components other than interferon present in the assay sample often influence viral growth. There is a need for a simple indirect interferon assay. Such an assay would find widespread application in at least three areas of interferon research:

(1) the monitoring of both laboratory and large-scale production and purification of interferon;

(2) the quantitation of interferon doses in research and clinical applications;

(3) the measurement of interferon in biological fluids.

The object of the present invention is to provide an antibody excess immuno assay for interferon which will fulfill this need.

The human body reacts to the presence of antigens by producing antibody molecules from its lymphocyte cells. Antibodies have the property of selectively binding to certain distinctive sites known as determinants on antibodies thereby rendering the antigen innocuous. The nature of the interaction between antigen and antibody is not fully understood but it is clear that antibodies have a physical affinity for specific determinants of antigenic material. A reaction between an antibody and a determinant on an antigen for which the antibody is specific results in an adduct, commonly referred to as an "immunocomplex". The formation of such species makes possible a wide variety of assays for antigenic material. Such assays are known generically as immuno assays.

Immunoassays fall broadly into two categories:

(1) Analyte excess; labelled antigen. (The term analyte is a term of art and in this context means "that to be analysed"). In this type of assay an antibody having specificity to the analyte is incubated with a solution containing the analyte and a known quantity of a labelled antigen. In this way a competitive equilibrium is set-up in which the unknown amount of analyte competes with the known amount of labelled antigen to form immunocomplexes with the antibody. A method of determining the number of immunocomplexes formed between labelled antigen and the antibody make it possible to deduce the amount of analyte. This type of assay has certain disadvantages in that the ultimate sensitivity of the assay is limited by the relative stability constants of the immunocomplexes formed.

(2) Antibody excess; labelled antibody. In this type of assay the analyte to be determined is incubated with an excess of labelled antibody molecules. The estimation of the amount of analyte is therefore linear and its maximum sensitivity is, in theory at least, one molecule of the analyte. A refinement of this method involves insolubilising an antibody to a solid substrate, in excess and allowing the analyte to form immunocomplexes therewith. Subsequently, an excess of labelled antibody to a second determinant on the analyte may be incubated with the solid substrate. This type of assay, commonly referred to as a "sandwich assay", adds a great deal of specificity to the immuno assay.

The present invention is particularly concerned with the second type of assay described, namely the antibody excess immunoassay, and is particularly applied to an assay for interferon.

According to the present invention reagents for performing an immunoassay for interferon comprise two antibodies to interferon, at least one of which is a monoclonal antibody, and one of which is a labelled antibody.

Conventional techniques for raising antibodies to interferon have proven problematical, because of the extremely small quantities of pure interferon available for immunisation in order to stimulate antibody production in animals. The low antigenicity and small quantities available can only produce antiserum of moderate purity. Research in the field of molecular biology has now provided an alternative source of antibodies. It has been discovered that fusion between lymphocyte cells and myeloma cells derived from mammals (for example, mice and rats) can produce hybrid cells capable of replication in vitro (see Kohler and Milstein, Nature 256, 495 to 597). Such hybrid cells have the property of secreting an antibody of predefined specificity. This specificity is that of the antibody produced by the lymphocyte involved in the fusion. The hybrid cells may be cloned and grown in stable culture to produce in the culture supernatant samples of antibody to a specific determinant. Antibodies produced in this way are known as monoclonal antibodies in the art.

The advantage of this technique is that it provides a source of a specific antibody uncontaminated by antibodies raised to other determinants either on the antigen with which the mammal was immunised or on antigen impurities in the immunising material. Another advantage of the technique is that antigen not available in the pure form for screening assays and present in the immunising material at low concentrations, for example interferon, may be used. Quite apart from the convenient source of antibody that the cell fusion techniques provides, the single determinant specificity of monoclonal antibodies has great ramifications in the field of immunoassay. In particular a monoclonal antibody will bind only one determinant. The antibodies previously used in immunoassay, commonly known as polyclonal antibodies, do not have this specificity and assays using such polyclonal antibodies were prone to inaccuracy as a result of this lack of specificity.

In one embodiment of the invention both antibodies to interferon are monoclonal antibodies.

A particularly suitable monoclonal antibody to interferon is the HU—IFNα—specific monoclonal antibody NK2, the isolation and properties of which are described in a paper by D. S. Secher and D. C. Burke, Nature 285 at page 446 to 450 (1980).

As mentioned, both antibodies to interferon may be monoclonal antibodies. Conveniently however one of the antibodies is a monoclonal antibody, e.g. NK2, and the other is an antibody raised by conventional techniques. Such conventionally-raised antibodies may be raised from humans, sheep, horse, mouse, goat, guinea-pig, chicken, rat etc. They will normally be purified as far as appropriate and modified, e.g. by blocking, in known manner, to enhance their specificity.

The assay may be carried out in the liquid phase or with the use of a solid support. If it is a liquid assay it may be a homogeneous assay, wherein no separation of the reactants is necessary, or a heterogeneous assay, wherein separation of the reactants must take place. Separation may be by means of an immunoprecipitation, by absorption by means of charcoal of the free antigen and antibody but not of the bound antigen-antibody complex, or by phase separation on the basis of different physical characteristics such as solubility.

The assay of the present invention is preferably carried out with the use of a solid support, to which the non-labelled antibody is initially attached. The assay may thus be performed in several ways, namely (a) reaction of the interferon antigen with excess of the solid-phase linked antibody followed by reaction of the product with the labelled antibody; (b) reaction of both the labelled antibody and the solid-phase linked antibody together with the antigen; and (c) reaction of the labelled antibody with the antigen followed by reaction with an excess of solid-phase linked antibody.

The solid support may be fixed or free. Examples of fixed supports are plates, tubes, trays and wells. Examples of free supports are beads, particles and powders. Typical materials from which the supports may be made include synthetic polymers, e.g. polystyrene, polyvinyl chloride, polyethylene, polyacrylamides, nylon and resins; natural polymers, e.g. cellulose, polysaccharides, sepharose, agarose, dextran; silica, glass, structural proteins such as collagen or polynucleotides, and cells, e.g. red blood cells, and *Staphylococcus aureus*. Attachment of the antibody to the solid support may be by absorption, adsorption, or by a covalent linkage, directly or by a linker.

The labelled monoclonal antibody may be isotopically or non-isotopically labelled. Preferably it is isotopically labelled, and the assay is thus an immunoradiometric assay (IRMA). The labelling may be direct or indirect (conjugate) and suitable labels include $^{125}I$, $^{131}I$, $^{32}P$, $^{14}C$ and $^{3}H$. Labelling techniques include the chloramine-T oxidation technique, the conjugation labelling technique (Bolton and Hunter, 1973b, Biochem. J 133,529), and the lactoperoxidase and iodogen procedures.

Non-isotopic labels which may be used in the assay of the present invention include enzymes, and the assay may thus be an enzyme immunoassay (EIA) or an enzyme linked immunosorbent assay (ELISA). Suitable enzyme markers include β-galactosidase, peroxidase, alkaline phosphatase, glucose oxidase etc. The assay may also be a fluorescent immunoassay (FIA), examples of markers being fluorophores such as fluoroscein, rhodamine and chelated rare earths. The assay may be a luminescent immunoassay (LIA) involving bioluminescent or chemiluminescent markers, e.g. luminol.

Other forms of non-isotopic labelling involve cell tagging, the use of heavy metals, co-enzymes, latex, free radicals and particle-counting (PACIA), all as known per se in the art.

The assay procedure is suitably conducted at temperatures in the range 4° to 37° C., preferably, at room temperature. When it includes two sequential incubations, the first may continue for 4 hours or so, the second for 8 to 16 hours, e.g. overnight.

DESCRIPTION OF DIAGRAMS

DETAILED DESCRIPTION OF THE EMBODIMENTS

As an example of a typical embodiment we describe an immunoradiometric assay (IRMA). In the assay to be described a sheep anti-interferon antibody is attached to a solid phase, polystyrene, and serves to anchor the interferon present in the sample to the solid phase. The bound interferon is then detected by the addition of $^{125}I$-NK2 (monoclonal anti-Hu-IFNα) and measurement of the counts bound to the solid phase.

The antibody NK2 was prepared as described by D. S. Secher and D. C. Burke in Nature, 285 at pages 446 to 450 (1980), and in International patent application No. PCT/GB 81/00067.

Three forms of polystyrene have been used as the solid phase.

(1) 3 ml test tubes (LP3, Luckham, Ltd., Bungers Hill, U.K.)

(2) 96-well microtiter trays (M24, Gibco Europe, Ltd. Uxbridge, U.K.)

(3) 6.5 mm beads (Northumbria Biologicals Ltd., Framlington, U.K.)

In the first case the whole tube was counted to measure the bound $^{125}I$-NK2. When trays were used the bottom of each well was cut off with a hot wire and transformed to a clean tube for counting. In the third case the beads were incubated in 20- or 60-well trays (93-0402, Abbott Laboratories, Basingstoke, U.K.) and transferred to tubes for counting. The incubation volumes used were 1 ml or 0.1 ml (wells) and 0.2 ml (beads). All three supports were found to be satisfactory and for assaying large numbers of samples the beads were preferred for their convenience.

NK2 antibody was purified from the serum and ascites fluid of mice carrying NK2 tumours by ammonium sulphate precipitation and DEAE ion-exchange chromatograph, labelled by the chloramine-T method and desalted on Sephadex G-50 (fine) column. The labelled IgG had a specific activity of about 2 Ci/μ mole or about 1 atom $^{125}I$ per molecule IgG.

In each assay a standard curve was constructed using either the interferon reference standard MRC 69/19 or a laboratory standard.

Figure 1:
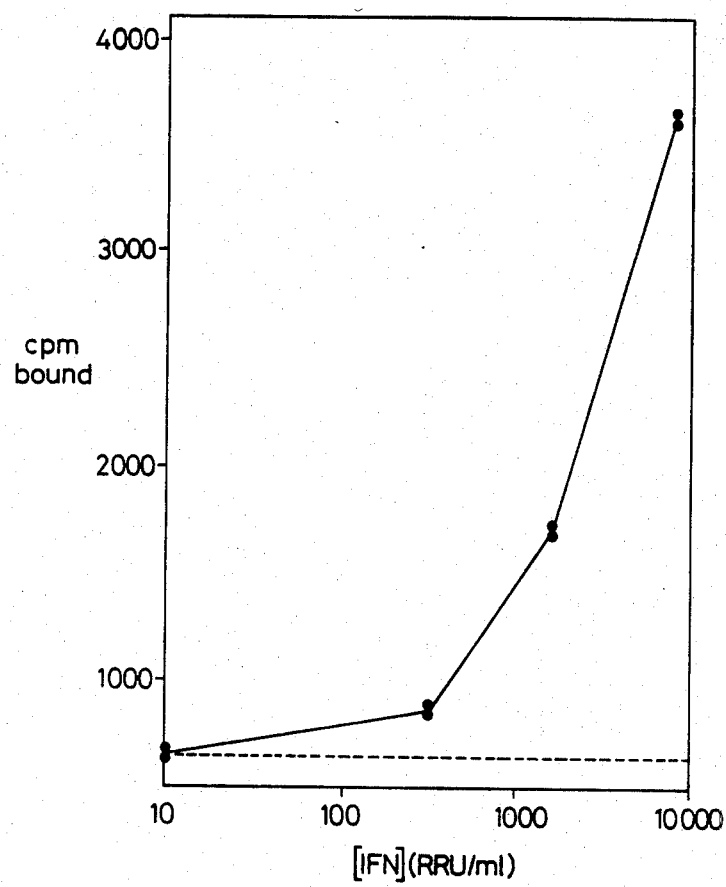
FIG. 1 is a standard curve for measurement of interferon by immunoassay.

In one such assay (see FIG. 1) IgG was purified from a sheep anti-Hu-IFNαantiserum (450,000 neutralising units/ml) by ammonium sulphate precipitation and DEAE-cellulose ion exchange chromatography and coated on to polystyrene beads by incubation of the beads at 4° C. for 16 hrs. in the sheep IgG (20 μg/ml in PBS—phosphate buffer solution—, 5 mM EDTA, 0.1%

NaN₃). Several hundred beads were coated, washed in a medium (HS medium) consisting of PBS, 10% horse serum, 0.1% NaN₃ and stored in HS medium at 4°. Assay trays (20- or 60-well, Abbott) were incubated with HS medium at 4° to block any sites for protein attachment. Interferon samples were diluted in HS medium and duplicate samples (200 μl) added to antibody-coated beads. After 4 h at 4° the beads were washed with 12 ml HS medium each using a combined dispenser/aspirator ("Pentwash", Abbott Laboratories). After removal of any residual medium, $^{125}$I-NK2 (purified IgG, 40,000 cpm) was added and incubated for 16 h at 4°. The beads were washed as before and transferred to a gamma-counter. The broken line indicates the background cpm bound when the coated beads were incubated in HS medium without interferon. The counts bound at 8,000 U/ml were at a maximum; no further increase was observed with interferon concentrations up to $10^6$ U/ml. The low level of non-specific binding (<1% of input counts is an important characteristic of the sandwich assay).

Figure 2:
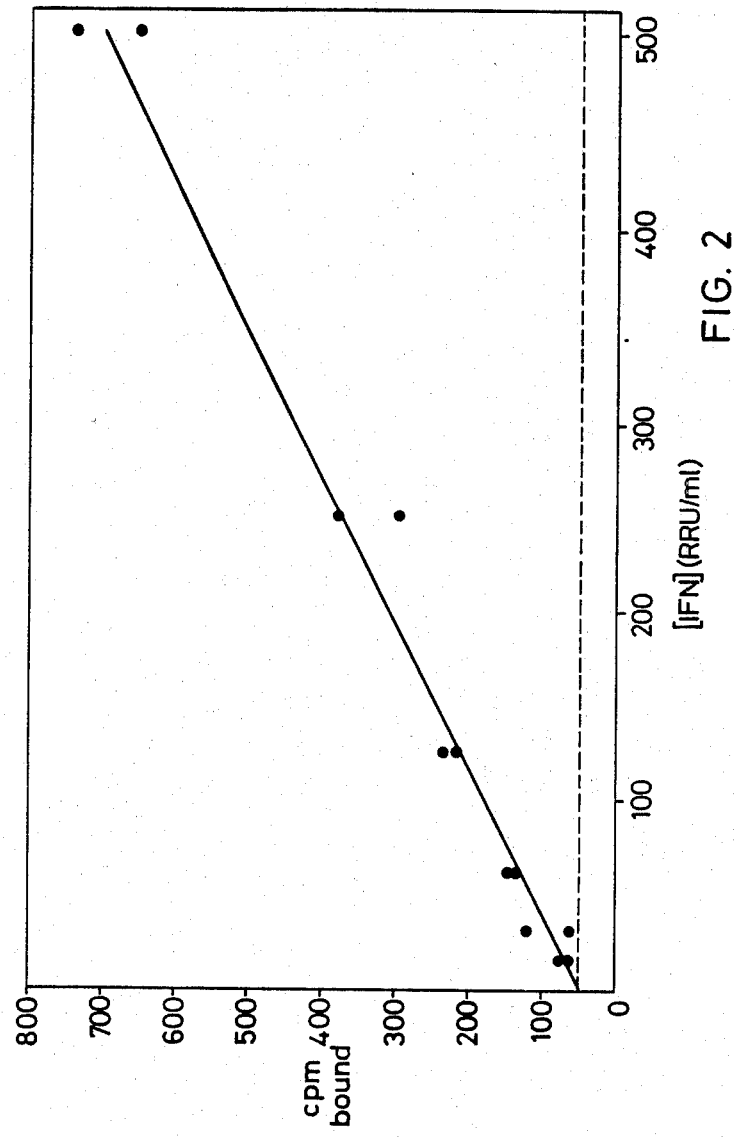
FIG. 2 is a standard curve for low levels of interferon.

In a second experiment (see FIG. 2) we showed that at low interferon concentrations the counts bound are proportional to the interferon concentration. Interferon samples were prepared by dilution of the reference research standard in HS medium and assayed as described for FIG. 1 except that only 23,000 cpm $^{125}$I-NK2 was added to each bead. The dotted line indicates the background cpm bound and was the mean of eight values (s.e. = ±6 cpm). It can be seen that concentrations of ≧50 U/ml can be easily measured. The standard assay conditions (i.e. those used in the construction of FIG. 1) have been adjusted for the convenient measurement of samples encountered in the purification of interferon. Such samples have values of $10^3$–$10^7$ U/ml. Solutions containing $10^3$ U/ml are diluted by serial dilution and the titration curve obtained matched to the standard curve. Comparison of the above immunoassay technique with the known antiviral assay technique on the same samples shows good agreement, with experimental error.

The immunoassay of the present invention offers considerable advantages over the conventional biological assay. Since the antibody-coated polystyrene can be used at 4°, samples can be assayed at short notice and the results are obtained within 24 hours of beginning the assay. The standard curves show very little variation from assay to assay compared to the much greater inherent variability of biological assays. Four measurements of a solution of 2000 U/ml gave a value of 3063±345 cpm in independent assays in which the input cpm ranged from 47000 to 53000 cpm. Only small amounts of sheep antibody are necessary, since the IgG solution used to coat the polystyrene can be re-used without apparently reducing the sensitivity of the assay. The quality of the sheep antibody is not a critical factor in the success of the assay, and other antibodies to Hu-IFNα, as described above, may substitute equally well. The assay exploits the specificity of the monoclonal antibody NK2 and since this is the product of a hybrid myeloma cell line in culture it can be produced in large amounts without any change in quality. Finally the assay is inexpensive (especially since all the plastic ware except the beads may be re-used), lends itself to automation and it is possible for one person to assay several hundred samples in a day.

Figure 3:
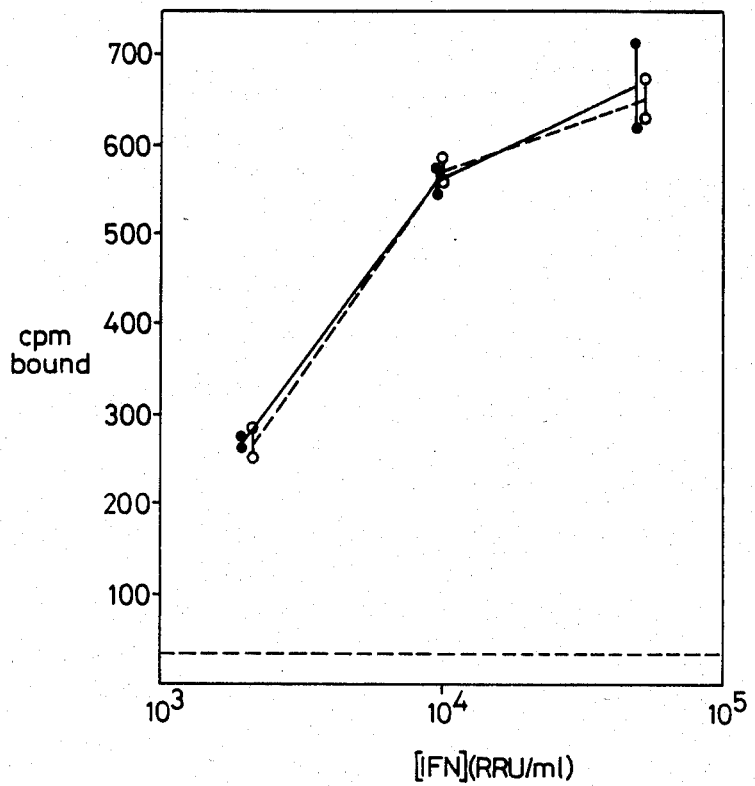
FIG. 3 is a graph representing interferon assay in the presence of human serum.

A limitation in the conventional assay of interferon in serum or other biological fluids has been the need to dilute the sample until the effects of other non-interferon substances that affect viral growth no longer mask the action of the interferon. Dilution of a sample of interferon purified by affinity chromatography on NK2-Sepharose in either PBS, 10% horse serum, 0.1% NaN₃ or in undiluted normal human serum resulted in the identical titration curves shown in FIG. 3 indicating that the immunoassay of the invention overcomes this problem. In this experiment interferon was (a) diluted in HS medium or (b) undiluted normal human serum and samples assayed as described in relation to FIG. 1 except that 3 ml test tubes were used as the polystyrene support rather than the beads. The solid line represents the cpm bound in case (a) and the broken line the results in case (b).

The lower limit in the measurement of serum interferon by biological assays has been sufficient to detect interferon in the serum of some patients to whom interferon has been administered. This sensitivity is insufficient, however, to measure the interferon concentration (if any) in normal human serum.

When conditions are adjusted to measure concentrations of interferon as described above the immunoassay of the invention can reliably measure around 50 U/ml. The sensitivity of the assay can moreover be further increased by prior concentration and purification of the interferon on a small NK-2-affinity column.

I claim:

1. An immunoassay for interferon involving an interferon antibody attached to a solid support, and a labelled monoclonal antibody, each of which antibodies is capable of specifically binding to at least one antigenic determinant of interferon, said process comprising the steps of:
   placing a sample to be assayed in contact with the solid support allowing immunocomplexes to form between interferon in the sample and the interferon antibody bound to the solid support,
   placing the labelled monoclonal antibody in contact with the solid support allowing immunocomplexes to form between interferon bound to the solid and the labelled monoclonal antibody, and
   estimating the immunocomplexes.

2. An immunoassay for interferon involving an interferon antibody attached to a solid support, and a labelled monoclonal antibody, each of which antibodies is capable of specifically binding to at least one antigenic determinant of interferon, said process comprising the steps of:
   reacting the labelled monoclonal antibody with the sample to be assayed,
   reacting the reaction product with an excess of the solid support linked antibody, and
   estimating the immunocomplexes formed.

3. An immunoassay for interferon involving an interferon antibody attached to a solid support, and a labelled monoclonal antibody, each of which antibodies is capable of specifically binding to at least one antigenic determinant of interferon, said process comprising the steps of:
   reacting the labelled monoclonal antibody and the solid support linked antibody with the sample to be assayed, and
   estimating the immunocomplexes formed.

4. An immunoassay as claimed in claim 1, wherein the labelled monoclonal antibody is derived from the NK2 cell line.

5. An immunoassay as claimed in claim 2, wherein the labelled monoclonal antibody is derived from the NK2 cell line.

6. An immunoassay as claimed in claim 3, wherein the labelled monoclonal antibody is derived from the NK2 cell line.

7. An immunoassay reagent kit for use in the assay of interferon comprising:
a first container containing a first antibody, and
a second container containing a second antibody, each of which antibodies is capable of specifically binding to an antigenic determinant of interferon, at least one of which antibodies is a monoclonal antibody and one of which antibodies is a labelled antibody.

8. A kit as claimed in claim 7 wherein the labelled antibody is a monoclonal antibody capable of specifically binding to a determinant of human interferon-α.

9. A kit as claimed in claim 8 wherein the monoclonal antibody is derived from the NK2 cell line.

10. A kit as claimed in claim 9 wherein the monoclonal antibody is a radio-labelled monoclonal antibody derived from the NK2 cell line.

11. A kit as claimed in claim 7 wherein both antibodies are monoclonal antibodies, one of which is labelled.

12. A kit as claimed in claim 7 wherein a non-labelled antibody is bound to a solid support.

13. An immunoassay reagent for use in the assay of interferon comprising
a first antibody, and
a second antibody each of which antibodies is capable of specifically binding to an antigenic determinant of interferon, at least one of which antibodies is a monoclonal antibody and one of which antibodies is a labelled antibody.

14. A reagent as claimed in claim 13 wherein the labelled antibody is a monoclonal antibody capable of specifically binding to a determinant of human interferon-α.

15. A reagent as claimed in claim 14 wherein the monoclonal antibody is derived from the NK2 cell line.

16. A reagent as claimed in claim 15 wherein the monoclonal antibody is a radio-labelled monoclonal antibody derived from the NK2 cell line.

17. A reagent as claimed in claim 13 wherein both antibodies are monoclonal antibodies, one of which is labelled.

18. A reagent as claimed in claim 13 wherein the non-labelled antibody is bound to a solid support.

* * * * *